US012784911B2

(12) United States Patent
Azizi et al.

(10) Patent No.: US 12,784,911 B2
(45) Date of Patent: Nov. 3, 2026

(54) SELF-SUPERVISED MACHINE LEARNING FOR MEDICAL IMAGE ANALYSIS USING CONTRASTIVE LOSS DERIVED FROM A DIFFERENCE OF IMAGE EMBEDDINGS TO MODIFY MACHINE LEARNING MODEL PARAMETERS

(71) Applicant: Google LLC, Mountain View, CA (US)

(72) Inventors: Shekoofeh Azizi, Vancouver (CA); Wen Yau Aaron Loh, Mountain View, CA (US); Zachary William Beaver, San Francisco, CA (US); Ting Chen, Toronto (CA); Jonathan Paul Deaton, San Mateo, CA (US); Jan Freyberg, London (GB); Alan Prasana Karthikesalingam, London (GB); Simon Kornblith, Toronto (CA); Basil Mustafa, Zürich (CH); Mohammad Norouzi, Toronto (CA); Vivek Natarajan, Sunnyvale, CA (US); Fiona Keleher Ryan, Atlanta, GA (US)

(73) Assignee: GOOGLE LLC, Mountain View, CA (US)

( * ) Notice: Subject to any disclaimer, the term of this patent is extended or adjusted under 35 U.S.C. 154(b) by 728 days.

(21) Appl. No.: 18/012,187

(22) PCT Filed: Dec. 10, 2021

(86) PCT No.: PCT/US2021/062857

§ 371 (c)(1),
(2) Date: Dec. 21, 2022

(87) PCT Pub. No.: WO2022/125930

PCT Pub. Date: Jun. 16, 2022

(65) Prior Publication Data

US 2023/0260652 A1 Aug. 17, 2023

Related U.S. Application Data

(60) Provisional application No. 63/124,254, filed on Dec. 11, 2020.

(51) Int. Cl.
*G06T 7/00* (2017.01)
*G06V 10/74* (2022.01)
(Continued)

(52) U.S. Cl.
CPC ........... *G16H 50/20* (2018.01); *G06T 7/0012* (2013.01); *G06V 10/761* (2022.01); *G16H 30/40* (2018.01);
(Continued)

(58) Field of Classification Search
CPC . G06T 2207/20081; G06T 2207/20132; G06T 7/0012; G16H 30/40; G16H 50/20;
(Continued)

(56) References Cited

U.S. PATENT DOCUMENTS

2021/0241037 A1* 8/2021 Lisowska .............. G06F 18/211
2021/0374553 A1* 12/2021 Li .......................... G06N 3/088

OTHER PUBLICATIONS

Lu et al. "Semi-Supervised Histology Classification using Deep Multiple Instance Learning and Contrastive Predictive Coding". Pub Date: Nov. 2, 2019. (Year: 2019).*

(Continued)

*Primary Examiner* — Chad Dickerson
(74) *Attorney, Agent, or Firm* — DORITY & MANNING P.A.

(57) ABSTRACT

Systems and methods can perform self-supervised machine learning for improved medical image analysis. As one example, self-supervised learning on ImageNet, followed by additional self-supervised learning on unlabeled medical images from the target domain of interest, followed by fine-tuning on labeled medical images from the target
(Continued)

domain significantly improves the accuracy of medical image classifiers such as, for example diagnostic models. Another example aspect of the present disclosure is directed to a novel Multi-Instance Contrastive Learning (MICLe) method that uses multiple different medical images that share one or more attributes (e.g., multiple images that depict the same underlying pathology and/or the same patient) to construct more informative positive pairs for self-supervised learning.

14 Claims, 10 Drawing Sheets

(51) Int. Cl.
*G16H 30/40* (2018.01)
*G16H 50/20* (2018.01)
*G16H 50/70* (2018.01)

(52) U.S. Cl.
CPC ... *G16H 50/70* (2018.01); *G06T 2207/20081* (2013.01); *G06T 2207/20132* (2013.01)

(58) Field of Classification Search
CPC ...... G16H 50/70; G06V 10/761; G06V 10/82; G06V 2201/03
USPC .......................................................... 382/128
See application file for complete search history.

(56) References Cited

OTHER PUBLICATIONS

Tellez et al. "Neural Image Compression for Gigapixel Histopathology Image Analysis". Pub Date: Apr. 15, 2020. (Year: 2020).*
Chaitanya et al. "Contrastive learning of global and local features for medical image segmentation with limited annotations" Pub Date: Oct. 30, 2020. Computer Vision Lab. pp. 1-10. "https://arxiv.org/pdf/2006.10511" (Year: 2020).*
Khosla et al. "Supervised Contrastive Learning". Pub Year: 2020 34th Conference on Neural Information Processing Systems. "https://dl.acm.org/doi/pdf/10.5555/3495724.3497291" (Year: 2020).*
Chen et al. "A Simple Framework for Contrastive Learning of Visual Representations". Pub Date: Jul. 1, 2020. Whole Document. "https://arxiv.org/pdf/2002.05709" (Year: 2020).*
International Search Report for Application No. PCT/US2021/062857, mailed on Mar. 31, 2022, 2 pages.
Ming, et al: "Semi-Supervised Histology Classification using Deep Multiple Instance Learning and Contrastive Predictive Coding", Arxiv.org, Cornell University Library, 201 Olin Library Cornell University, Ithaca, NY 14853, Oct. 24, 2019 (Oct. 24, 2019), XP081527323, 8 pages.
Tellez, et al: "Neural Image Compression for Gigapixel Histopathology Image Analysis", IEEE Transactions On Pattern Analysis And Machine Intelligence, IEEE Computer Society, USA, vol. 43, No. 2, Aug. 22, 2019 (Aug. 22, 2019), 15 pages.
International Preliminary Report on Patentability for Application No. PCT/US2021/062857, mailed Jun. 22, 2023, 10 pages.

* cited by examiner

SELF-SUPERVISED MACHINE LEARNING FOR MEDICAL IMAGE ANALYSIS USING CONTRASTIVE LOSS DERIVED FROM A DIFFERENCE OF IMAGE EMBEDDINGS TO MODIFY MACHINE LEARNING MODEL PARAMETERS

PRIORITY CLAIM

This application is based on and claims the right of priority under 35 U.S.C. § 371 to International Application No. PCT/US2021/062857 filed on Dec. 10, 2021, which claims priority to and the benefit of U.S. Provisional Patent Application No. 63/124,254, filed Dec. 11, 2020. Applicant claims priority to and the benefit of each of such applications and incorporates all such applications herein by reference in their entirety.

FIELD

The present disclosure relates generally to machine learning. More particularly, the present disclosure relates to systems and methods that perform self-supervised machine learning for improved medical image analysis.

BACKGROUND

The success of various image analysis tasks (e.g., image classification) is often a function of the amount of labeled data available. However, annotating a large set of images with class labels is time-consuming and expensive, especially in the medical field. To mitigate the shortage of labeled data, a common strategy entails supervised pretraining on a large, labeled dataset such as ImageNet, followed by supervised fine-tuning on a specific target dataset. Recently, self-supervised pretraining of representations using contrastive learning have provided strong results for natural images (e.g., photographs or other images which depict common real world scenes and may be captured using commonly-available cameras).

Medical images can include images captured specifically for or in the medical context and which may in some but not all instances require specialized imaging equipment. Medical images are often significantly different from natural images and therefore raise additional challenges. As examples: medical images can be of significantly higher resolution than natural images; medical images may have certain color channels missing; and/or medical images may also exhibit much smaller texture variations across the image as a whole. Furthermore, classification of medical images may occur relative to a label space which is significantly smaller and exhibits much greater label uncertainty as compared to natural images. These attributes of medical images render it challenging to take typical approaches for natural images and directly apply them to medical imagery.

SUMMARY

Aspects and advantages of embodiments of the present disclosure will be set forth in part in the following description, or can be learned from the description, or can be learned through practice of the embodiments.

One example aspect of the present disclosure is directed to a computing system to perform multi-instance contrastive learning for improved analysis of medical imagery. The computing system includes one or more processors and one or more non-transitory computer-readable media that collectively store instructions that, when executed by the one or more processors, cause the computing system to perform operations. The operations include obtaining, by the computing system, a set of medical training images that comprises a plurality of patient-specific image subsets, wherein each patient-specific image subset contains a plurality of different images that depict a same respective patient. The operations include, for each of the plurality of patient-specific image subsets: obtaining, by the computing system, a first medical image that depicts a patient and a second, different medical image that depicts the same patient; processing, by the computing system, the first medical image with a machine-learned medical image analysis model to generate a first embedding for the first medical image; processing, by the computing system, the second medical image with the machine-learned medical image analysis model to generate a second embedding for the second medical image; and modifying, by the computing system, one or more values of one or more parameters of the machine-learned medical image analysis model based at least in part on a loss function that evaluates a difference between the first embedding for the first medical image and the second embedding for the second medical image.

Another example aspect of the present disclosure is directed to a computer-implemented method to train machine learning models for improved analysis of medical imagery. The method includes obtaining, by a computing system comprising one or more computing devices, a set of unlabeled medical training images and a set of labeled medical training images. The method includes performing, by the computing system, a self-supervised learning technique to train a machine-learned medical image analysis model with the set of unlabeled medical training images. The method includes after performing the self-supervised learning technique, performing, by the computing system, a supervised learning technique to train the machine-learned medical image analysis model with the set of labeled medical training images. The method includes, after performing the supervised learning technique, providing, by the computing system, the machine-learned medical image analysis model as a trained output.

Another example aspect of the present disclosure is directed to one or more non-transitory computer-readable media that collectively store instructions that, when executed by a computing system comprising one or more computing devices, cause the computing system to perform operations. The operations include obtaining, by the computing system, a set of medical training images that comprises a plurality of attribute-specific image subsets, wherein each attribute-specific image subset contains a plurality of different images that share a common attribute. The operations include for each of the plurality of attribute-specific image subsets: obtaining, by the computing system, a first medical image and a second, different medical image that have the common attribute; processing, by the computing system, the first medical image with a machine-learned medical image analysis model to generate a first embedding for the first medical image; processing, by the computing system, the second medical image with the machine-learned medical image analysis model to generate a second embedding for the second medical image; and modifying, by the computing system, one or more values of one or more parameters of the machine-learned medical image analysis model based at least in part on a loss function that evaluates a difference between the first embedding for the first medical image and the second embedding for the second medical image.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which.

Figure 1A:
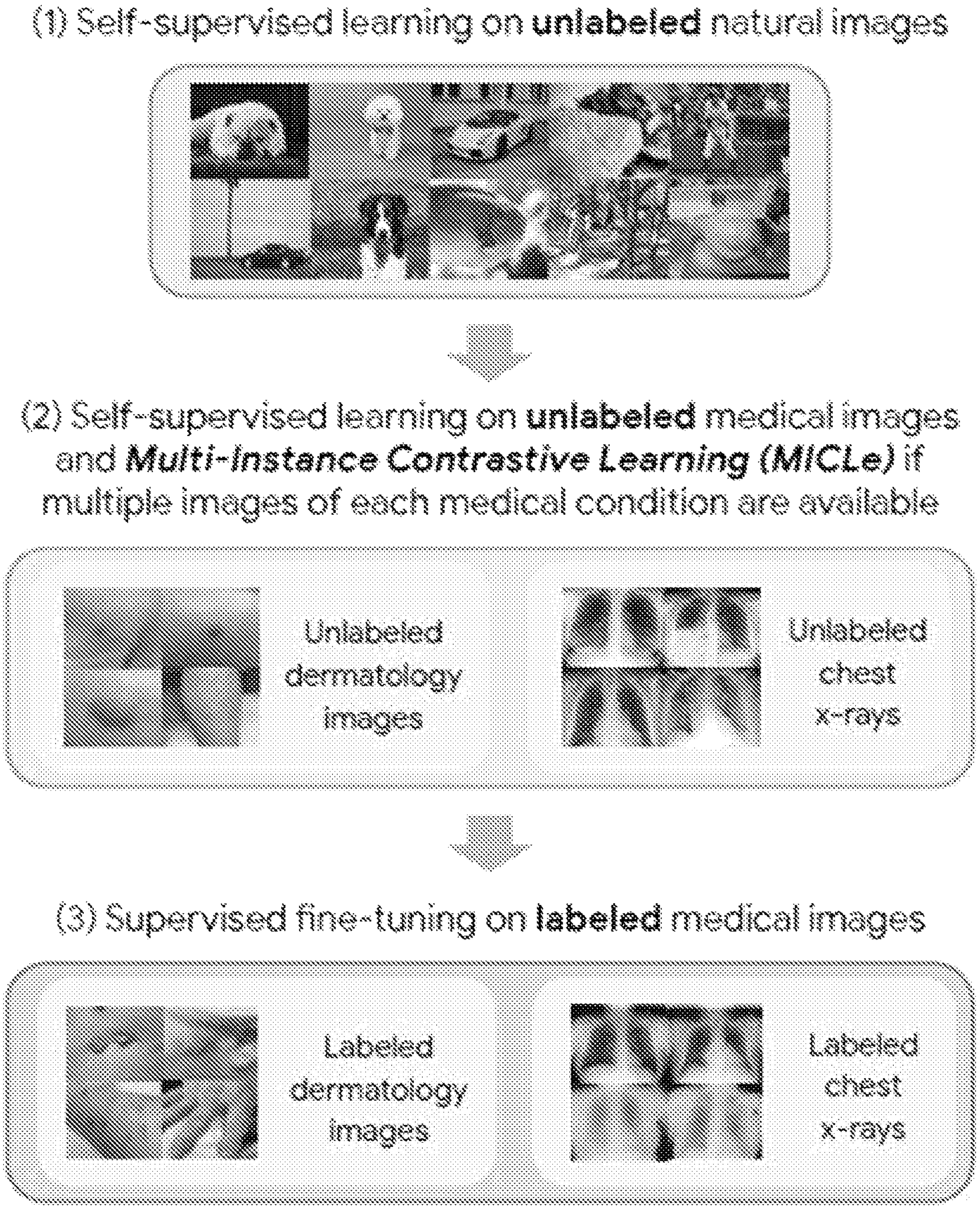
FIG. 1A depicts a graphical flow diagram of an example process for training a machine-learned medical image analysis model according to example embodiments of the present disclosure.

Reference numerals that are repeated across plural figures are intended to identify the same features in various implementations.

DETAILED DESCRIPTION

Overview

Generally, the present disclosure is directed to systems and methods that perform self-supervised machine learning for improved medical image analysis. As one example, self-supervised learning on ImageNet, followed by additional self-supervised learning on unlabeled medical images from the target domain of interest, followed by fine-tuning on labeled medical images from the target domain significantly improves the accuracy of medical image classifiers such as, for example diagnostic models. Another example aspect of the present disclosure is directed to a novel Multi-Instance Contrastive Learning (MICLe) method that uses multiple different medical images that share one or more attributes (e.g., multiple images that depict the same underlying pathology and/or the same patient) to construct more informative positive pairs for self-supervised learning. As described in U.S. Provisional Patent Application No. 63/124,254, example implementations of these approaches achieve an improvement of 6.4% in top-1 accuracy and an improvement of 1.4% in mean AUC, respectively, on two distinct tasks: dermatology skin condition classification from digital camera images and multi-label chest X-ray classification, outperforming strong supervised baselines pretrained on ImageNet. In addition, example experiments contained in U.S. Provisional Patent Application No. 63/124,254 show that big self-supervised models are robust to distribution shift and can learn efficiently with a small number of labeled medical images.

More particularly, the present disclosure provides systems and methods for self-supervised learning for medical image analysis. It is observed that self-supervised pretraining outperforms supervised pretraining even when the full ImageNet dataset (14 M images and 21.8K classes) is used for the latter. This finding is attributable to the domain shift and discrepancy between the nature of recognition tasks in ImageNet and medical image classification tasks. Self-supervised approaches bridge this domain gap by leveraging in-domain medical data for pretraining and they also scale gracefully as they do not require any form of class label annotation.

One example aspect provided by the present disclosure is a novel Multi-Instance Contrastive Learning (MICLe) strategy that helps adapt contrastive learning to multiple different medical images that share a common attribute (e.g., depict the same pathology and/or the same patient). Such multi-instance data is often available in medical imaging datasets—e.g., frontal and lateral views of chest x-rays/mammograms, retinal fundus images from each eye, etc. Given multiple images that share a common attribute, example implementations of the present disclosure can construct a positive pair for self-supervised contrastive learning from the images (e.g., by drawing two crops from the two distinct images or otherwise optionally augmenting the images). The multiple different medical images that share a common attribute may be taken from different viewing angles, under different lighting conditions, at different times (e.g., at different care visits), and/or show different body parts (e.g., with the same underlying pathology). This presents a great opportunity for self-supervised learning algorithms to learn representations that are robust to changes of viewpoint, imaging conditions, and other confounding factors in a direct way. MICLe does not require class label information and only relies on different images which are known to share a common attribute (e.g., which may or may not be directly related to the ultimate task at hand).

The systems and methods of the present disclosure provide a number of technical effects and benefits. As one example, the present disclosure investigates the choice of datasets for self-supervised pretraining and demonstrates that pretraining on ImageNet is complementary to pretraining on unlabeled medical images, i.e., best results are achieved when both are combined.

As another example technical effect, the present disclosure provides Multi-Instance Contrastive Learning (MICLe to leverage the potential availability of multiple images per medical condition. MICLe significantly improves the accuracy of skin condition classification, yielding state-of-the-art results on this dataset. Thus, the proposed MICLe technique improves the performance of a diagnostic model, potentially leading to improved and/or more efficient healthcare outcomes.

U.S. Provisional Patent Application No. 63/124,254 also includes careful empirical studies on two distinct datasets which suggest that self-supervised pretraining often outperforms supervised pretraining on ImageNet. Self-supervised pretraining is particularly effective in the semi-supervised setting, when additional unlabeled examples are available for pretraining. In this setting, baseline performance is matched using only 20% of the available labels for the dermatology task. Thus, the proposed approaches enable improved model performance when only a small amount of labels are available, which may permit use for detection of rare or otherwise low representation pathologies.

Thus, the systems and methods described herein can result in improved model and system performance. For example, example combinations of the proposed approaches achieve an improvement of 6.4% in top-1 accuracy on the dermatology skin condition classification task and an improvement of 1.4% in mean AUC on chest x-ray classification, outperforming strong supervised baselines pre-trained on ImageNet.

The present disclosure also demonstrates that self-supervised models are robust and generalize better than baselines when subjected to shifted test sets, without fine-tuning. Such behavior is desirable for deployment in a real-world clinical setting. Stated differently, robust models which generalize better than baselines are less susceptible to inaccurate diagnoses when applied to different demographics or in different settings (e.g., for different imaging equipment).

With reference now to the Figures, example embodiments of the present disclosure will be discussed in further detail.

Example Training Configurations

FIG. 1A depicts a graphical flow diagram of an example process for training a machine-learned medical image analysis model according to example embodiments of the present disclosure. In particular, one example approach according to aspects of the present disclosure can include three steps: First, self-supervised pretraining can be optionally performed on unlabeled natural images (e.g., such as those contained in the ImageNet dataset). For example, the self-supervised pretraining performed on the natural images can include contrastive learning techniques or other self-supervised tasks that define a self-supervised pretext task.

Example self-supervised techniques that can be performed on the natural images and which define a self-supervised pretext task include Exemplar-CNN (Dosovitskiy et al., Discriminative Unsupervised Feature Learning with Exemplar Convolutional Neural Networks 2015 arXiv: 1406.6909); rotation of an entire image (see, e.g., Gidaris et al. Unsupervised Representation Learning by Predicting Image Rotations 2018 arXiv:1803.07728); predicting the relative position between two patches of an image (see, e.g., Doersch et al. Unsupervised Visual Representation Learning by Context Prediction 2015 arXiv:1505.05192); solving a jigsaw puzzle generated from the image (see, e.g., Noroozi & Favaro Unsupervised Learning of Visual Representations by Solving Jigsaw Puzzles 2016 arXiv:1603.09246); colorization pretext tasks (see, e.g., Zhang et al. Colorful Image Colorization, 2016, arXiv:1603.08511); and/or other self-supervised techniques.

Example contrastive self-supervised methods that can be performed include: instance discrimination (Wu et al. Unsupervised feature learning via non-parametric instance discrimination. In *Proceedings of the IEEE Conference on Computer Vision and Pattern Recognition*, pages 3733-3742, 2018); CPC (Olivier J Henaff, Aravind Srinivas, Jeffrey De Fauw, Ali Razavi, Carl Doersch, S M Eslami, and Aaron van den Oord. Data-efficient image recognition with contrastive predictive coding. arXiv preprint arXiv: 1905.09272, 2019 and Aaron van den Oord, Yazhe Li, and Oriol Vinyals. Representation learning with contrastive predictive coding. arXiv preprint arXiv:1807.03748, 2018); Deep InfoMax (R Devon Hjelm, Alex Fedorov, Samuel Lavoie-Marchildon, Karan Grewal, Phil Bachman, Adam Trischler, and Yoshua Bengio. Learning deep representations by mutual information estimation and maximization. 2019); invariant and spreading instance feature learning (Ye et al. Unsupervised embedding learning via invariant and spreading instance feature. In *Proceedings of the IEEE Conference on computer vision and pattern recognition*, pages 6210-6219, 2019); AMDIM (Philip Bachman, R Devon Hj elm, and William Buchwalter. Learning representations by maximizing mutual information across views. In Advances in Neural Information Processing Systems, pages 15535-15545, 2019); CMC (Yonglong Tian, Dilip Krishnan, and Phillip Isola. Contrastive multiview coding. arXiv preprint arXiv:1906.05849, 2019); MoCo (Kaiming He, Haoqi Fan, Yuxin Wu, Saining Xie, and Ross Girshick. Momentum contrast for unsupervised visual representation learning. In *Proceedings of the IEEE/CVF Conference on Computer Vision and Pattern Recognition*, pages 9729-9738, 2020 and Xinlei Chen, Haoqi Fan, Ross Girshick, and Kaiming He. Improved baselines with momentum contrastive learning. arXiv preprint arXiv:2003.04297, 2020); PIRL (Ishan Misra and Laurens van der Maaten. Self-supervised learning of pretext-invariant representations. In *Proceedings of the IEEE/CVF Conference on Computer Vision and Pattern Recognition*, pages 6707-6717, 2020); and SimCLR (Ting Chen, Simon Kornblith, Mohammad Norouzi, and Geoffrey Hinton. A simple framework for contrastive learning of visual representations. arXiv preprint arXiv:2002.05709, 2020 and Ting Chen, Simon Kornblith, Kevin Swersky, Mohammad Norouzi, and Geoffrey Hinton. Big self-supervised models are strong semi-supervised learners. arXiv preprint arXiv:2006.10029, 2020). Additional example self-supervised contrastive learning techniques which can be performed are described in U.S. patent application Ser. No. 17/018,372, which is hereby incorporated by reference in its entirety.

SimCLR learns representations by maximizing agreement (see, e.g., Suzanna Becker and Geoffrey E Hinton. Self-organizing neural network that discovers surfaces in random-dot stereograms. Nature, 355(6356):161-163, 1992) between differently augmented views of the same data example via a contrastive loss in a hidden representation of neural nets. Given a randomly sampled mini-batch of images, each image $x_i$ is augmented a number of times (e.g., twice) using random crop, color distortion and Gaussian blur, creating two views of the same example $x_{2k-1}$ and $x_{2k}$. The two images are encoded via an encoder network $f(\cdot)$ (e.g., a ResNet) to generate representations $h_{2k-1}$ and $h_{2k}$. The representations are then transformed again with a non-linear transformation network $g(\cdot)$ (a MLP projection head), yielding $z_{2k-1}$ and $z_{2k}$ that are used for the contrastive loss.

With a mini-batch of encoded examples, the contrastive loss between a pair of positive example i; j (e.g., augmented images generated from the same original image) can be given as follows:

$$\ell_{i,j}^{NT-X_{ent}} = -\log \frac{\exp(sim(z_i, z_j)/\mathcal{T})}{\sum_{k=1}^{2N} \mathbb{1}_{[k \neq i]} \exp(sim(z_i, z_k)/\mathcal{T})}, \quad (1)$$

Where sim (·; ·) is a similarity measure (e.g., cosine similarity) between two vectors, and $\tau$ is a temperature scalar.

In a second training stage, additional self-supervised pretraining can be performed using a set of unlabeled medical images. For example, any of the self-supervised training techniques described above with respect to the first training stage can again be performed on a set of unlabeled training images.

The set of unlabeled training images can include images captured specifically for or in the medical context and which may in some but not all instances require specialized imaging equipment. As examples, the set of unlabeled medical training images can include: dermatological images, radiographic images, endoscopic images, ultrasound images, mammographic images, pathology images, posterior eye images, or three-dimensional scan images (e.g., 3D CT or MRI scans).

Figure 1B:
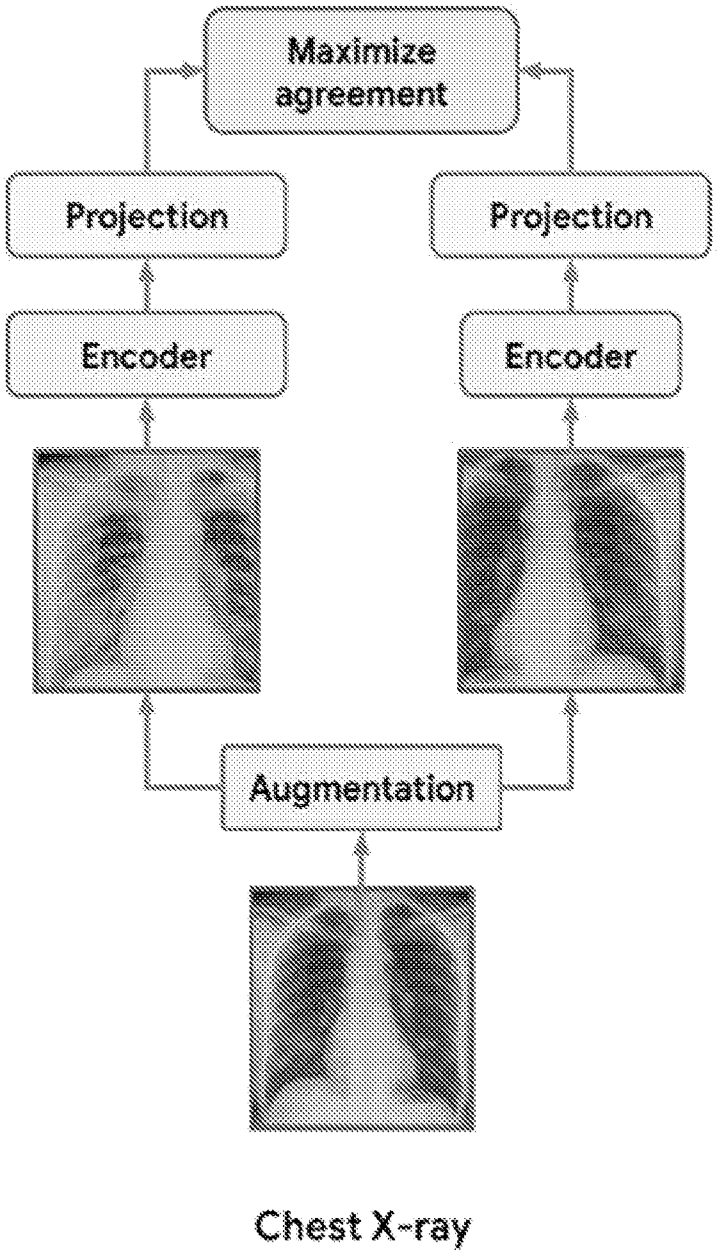
FIG. 1B depicts a graphical flow diagram of an example process for performing contrastive learning with a radiographic image according to example embodiments of the present disclosure.
Figure 1C:
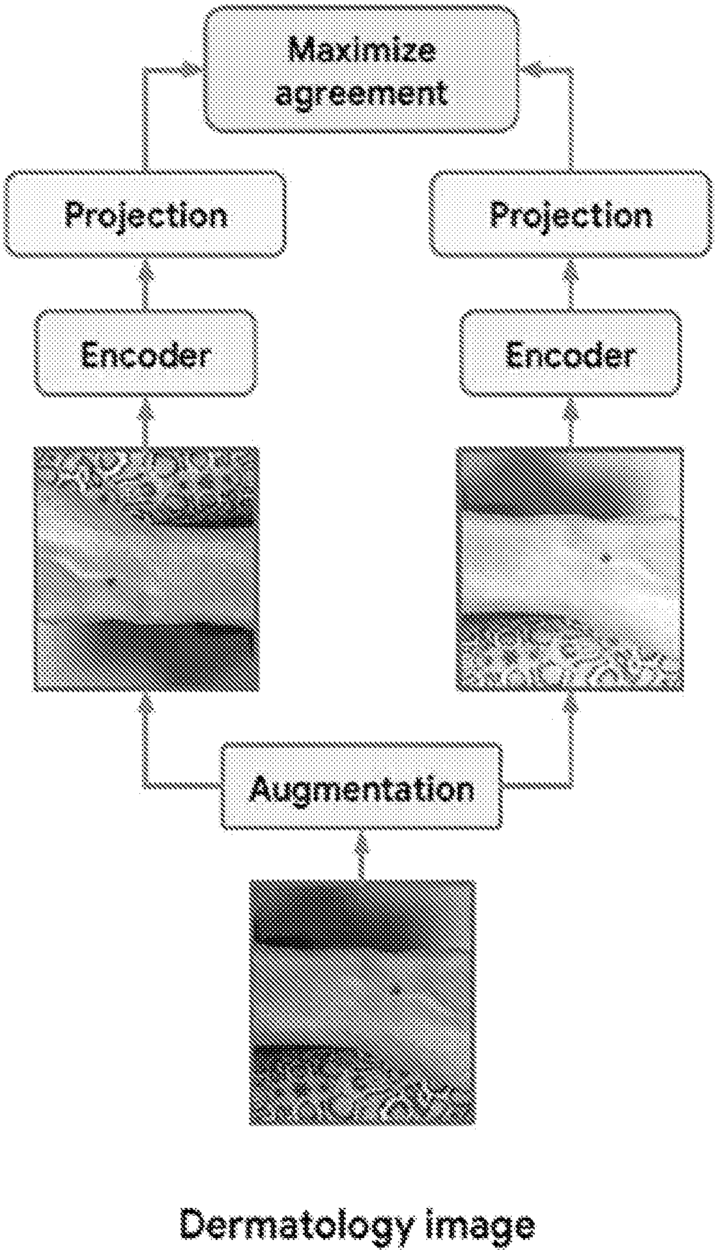
FIG. 1C depicts a graphical flow diagram of an example process for performing contrastive learning with a dermatological image according to example embodiments of the present disclosure.

As one example, FIG. 1B depicts a graphical flow diagram of an example process for performing contrastive learning with a radiographic image according to example embodiments of the present disclosure. As another example, FIG. 1C depicts a graphical flow diagram of an example process for performing contrastive learning with a dermatological image according to example embodiments of the present disclosure. In each of FIGS. 1B and 1C, data augmentation can be applied to a single medical image to generate two augmented views of the same image. The model can be trained to maximize two respective representations or embeddings generated for the two augmented views.

Referring again to FIG. 1A, in some implementations, if multiple attribute-specific images are available, a novel Multi-Instance Contrastive Learning (MICLe) can optionally be used to construct more informative positive pairs based on different images. These positive pairs can be used at the second stage of training to perform additional or alternative self-supervised training.

More particularly, in medical image analysis, it is common to utilize multiple images per patient to improve classification accuracy and robustness. Such images may be taken from different viewpoints or under different lighting conditions, providing complementary information for medical diagnosis.

Thus, when multiple images of a medical condition and/or a patient and/or some other common medically-relevant attribute are available as part of the training dataset, example implementations of the present disclosure can learn representations that are invariant not only to different augmentations of the same image, but also to different images of the same medical pathology.

Figure 1D:
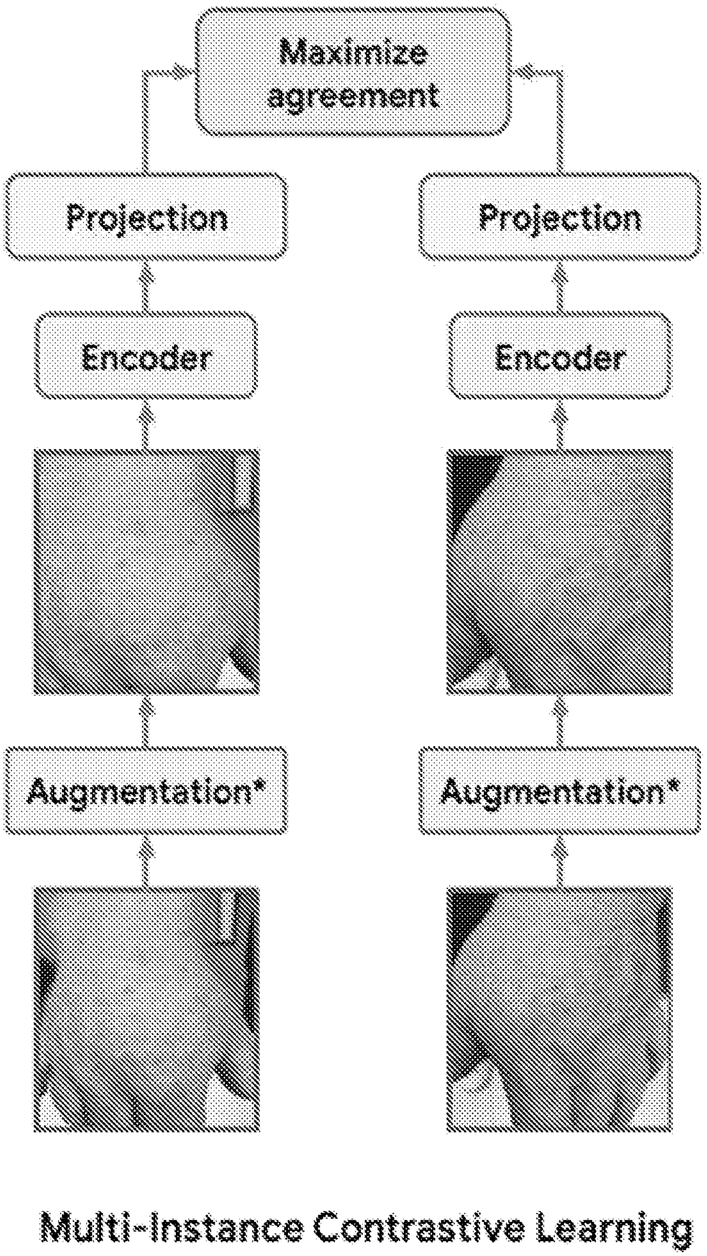
FIG. 1D depicts a graphical flow diagram of an example process for performing multi-instance contrastive learning with multiple different images that depict the same patient according to example embodiments of the present disclosure.

Accordingly, after pretraining with standard SimCLR on two augmented views of each image, another self-supervised learning stage can be conducted where positive pairs are constructed by drawing two crops from two different images which share a common attribute. As one example, the two images can be two images of the same patient as demonstrated in FIG. 1D. In this case, the objective can still take the form of Eq. (1), but images contributing to each positive pair are distinct. As used herein, the term patient can refer to any specific individual (e.g., person).

In standard SimCLR to construct a minibatch of 2N representations, one uses N images each of which is augmented twice. In MICLe, a minibatch of N pairs of related images can be used. In addition, and since the images are distinct, a lightweight data augmentation (or no augmentation at all) can be used.

Leveraging multiple images that share a common attribute (e.g., that depict the same condition and/or patient) using the contrastive loss helps the model learn representations that are more robust to the change of viewpoint, lighting conditions, and other confounding factors. As a result, multi-instance contrastive learning significantly improves the accuracy and helps the trained models to achieve the state-of-the-art result on the dermatology condition classification task.

Referring again to FIG. 1A, in a third stage of training, fine-tuning (e.g., supervised fine-tuning) can be performed using a set of labeled medical images. Note that unlike the first step, both the second and third steps are typically task and dataset specific. The fine-tuning task can any number of different image analysis tasks, including as examples, classification (e.g., diagnostic classification); segmentation (e.g., for attribution purposes); image retrieval; object detection; image registration; etc.

Example Telemedicine Configurations

Figure 2A:
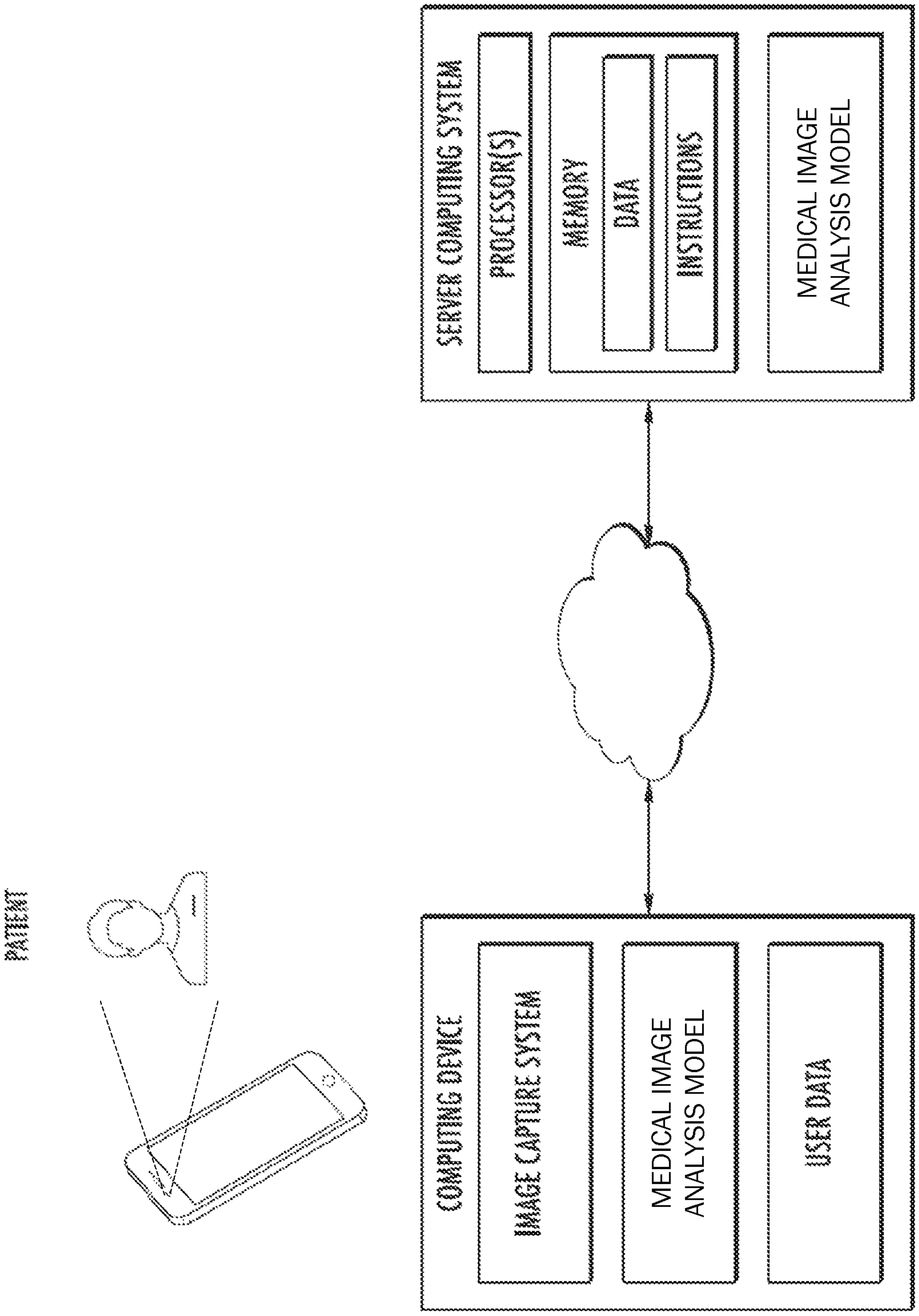
FIG. 2A depicts an example block diagram of a system for analyzing medical imagery according to example embodiments of the present disclosure.

FIG. 2A depicts an example client-server environment according to example embodiments of the present disclosure. Specifically, FIG. 2A depicts a user computing device and a server system that communicate over a network. The computing device can be a personal electronic device such as a smartphone, tablet, laptop, and so on. The computing device can include an image capture system, at least a portion of a medical image analysis model, and user data. The image capture system can capture one or more images of a patient.

In some implementations, the computing device can transmit the captured image(s) to the server computing device. Alternatively or additionally, the medical image analysis model can include at least a portion of the medical image analysis model that generates embeddings for one or more images. In this way, the computing device can transmit an embedding representing the image, rather than the image itself. This can reduce the amount of bandwidth needed to transmit the images to the server computing system.

The user data can be stored in a local data storage device and can include user clinical data, user demographic data, and/or user medical history data. This information can be transmitted to the server computing system as needed with user permission. In some examples, the medical image analysis model at the user computing device can include a context component that generates a feature representation for the user data. In some examples, the medical image analysis model can combine one or more image embeddings and the feature representation data for the user data.

The server computing system includes some or all of a medical image analysis model. For example, the server computing system can receive one or more of: image data, one or more embeddings, a unified image representation of multiple embeddings, a feature representation of user data, or a combined representation of unified image representations and a feature representation. Any and/or all of these types of data can be received at the server computing system and used to generate one or more output such as disease detections or other diagnostic predictions. The model outputs can be transmitted to the computing device or to another third-party device as needed and approved by the user.

Figure 2B:
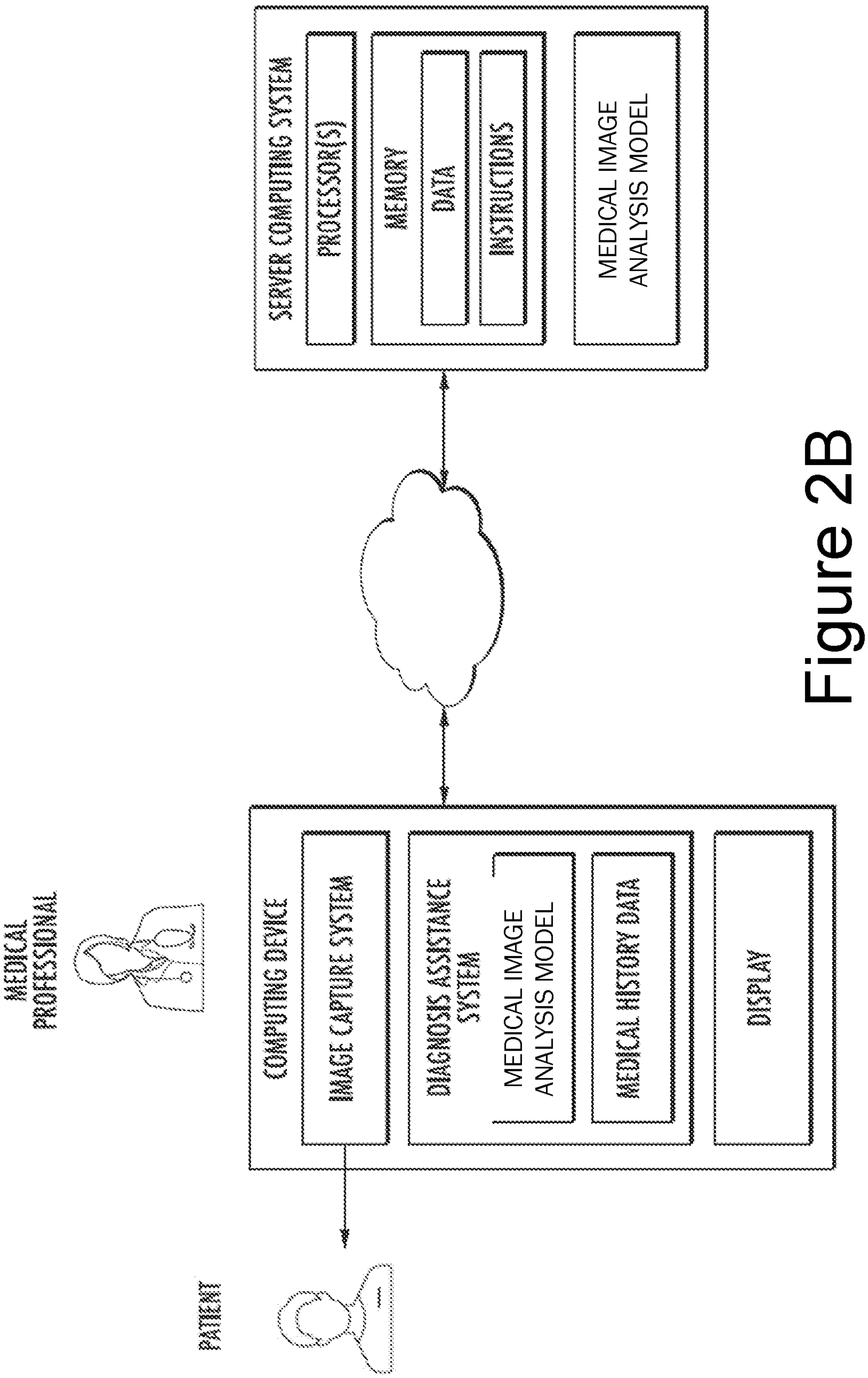
FIG. 2B depicts an example block diagram of a system for analyzing medical imagery according to example embodiments of the present disclosure.

FIG. 2B depicts an example block diagram of a system for providing diagnosis assistance according to example embodiments of the present disclosure. In this example, the computing device is associated with a medical professional (e.g., a doctor (e.g., optometrist, ophthalmologist, radiologist, dermatologist, etc.), a nurse practitioner, and so on). The medical professional can utilize the computing device to obtain aid during their diagnostic process. The computing device can include an image capture system (e.g., a camera and associated software), a diagnosis assistance system, and a display. The diagnosis assistance system can include some or all of a medical image analysis model and medical history data.

The medical professional can use the computing device to capture one or more images of the patient using the image capture system. The diagnosis assistance system can process the imagery locally, generate embeddings locally, or transmit the raw image data to the server computing system. Similarly, medical history data can be processed locally to generate a feature representation or transmitted to the server computing system. In some examples, the diagnosis assistance system includes the full medical image analysis model and thus can generate disease detections without transmitting data to the server computing system.

In some examples, the diagnostic assistance system transmits data to the server computing system. The medical image analysis model at the server computing system can generate one or more outputs such as disease detections or other diagnostic predictions and transmit the data back to the diagnosis assistance system for display to the medical professional in the display at the computing device.

Figure 2C:
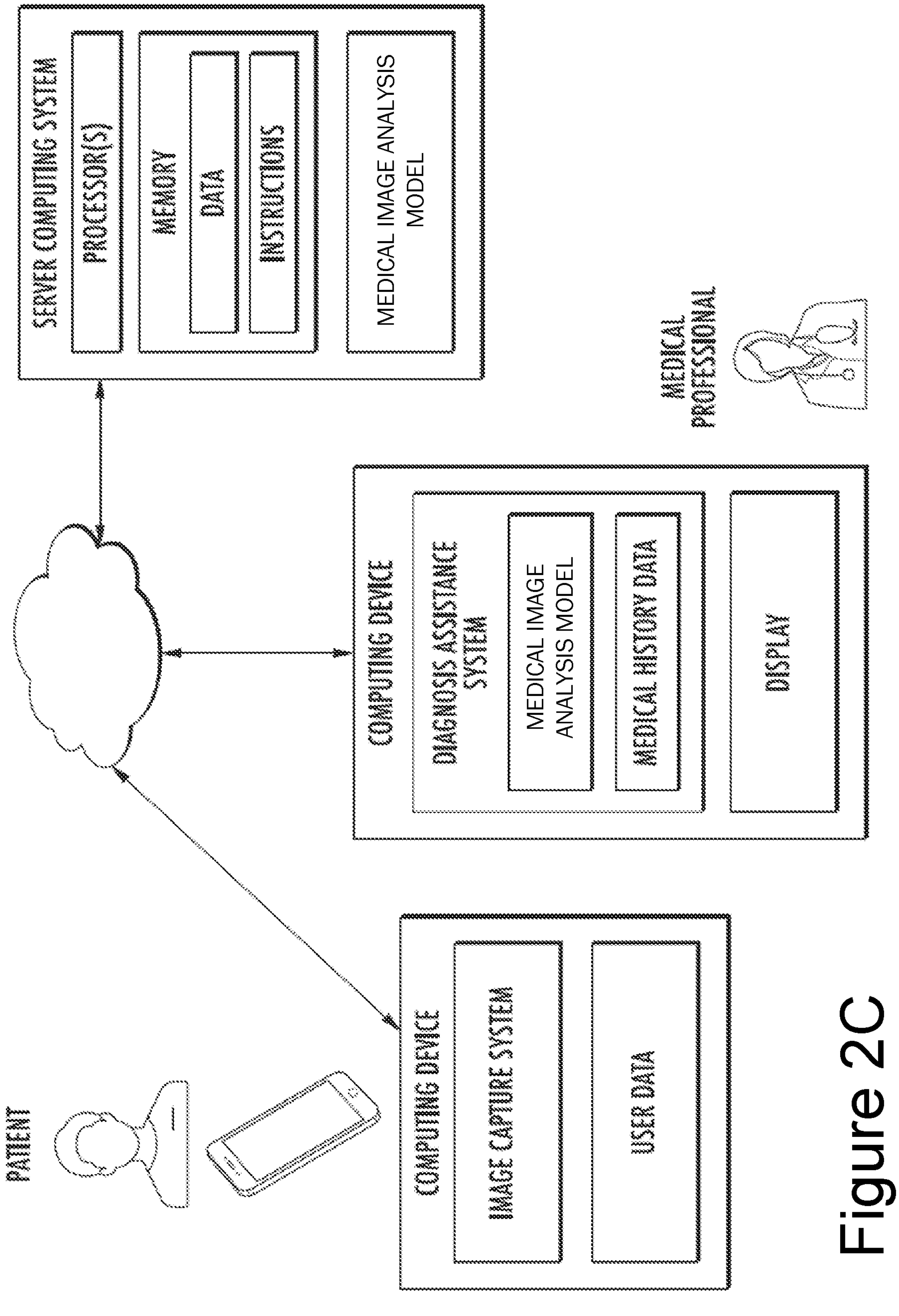
FIG. 2C depicts an example block diagram of a system for analyzing medical imagery according to example embodiments of the present disclosure.

FIG. 2C depicts an example block diagram of a system for providing diagnosis assistance according to example embodiments of the present disclosure. In this example, the patient is not physically present with the medical professional. Instead, the patient uses a computing device with an image capture system to transmit one or more images (and potentially user data) to the computing device associated with the medical professional and/or the server computing system via a network. Once the computing device receives the one or more images from the computing device associated with the patient, the process can proceed as described above with respect to FIG. 2A or 2B. The medical professional can then transmit any relevant outputs such as diagnostic information to the computing device of the patient.

Example Devices and Systems

Figure 3A:
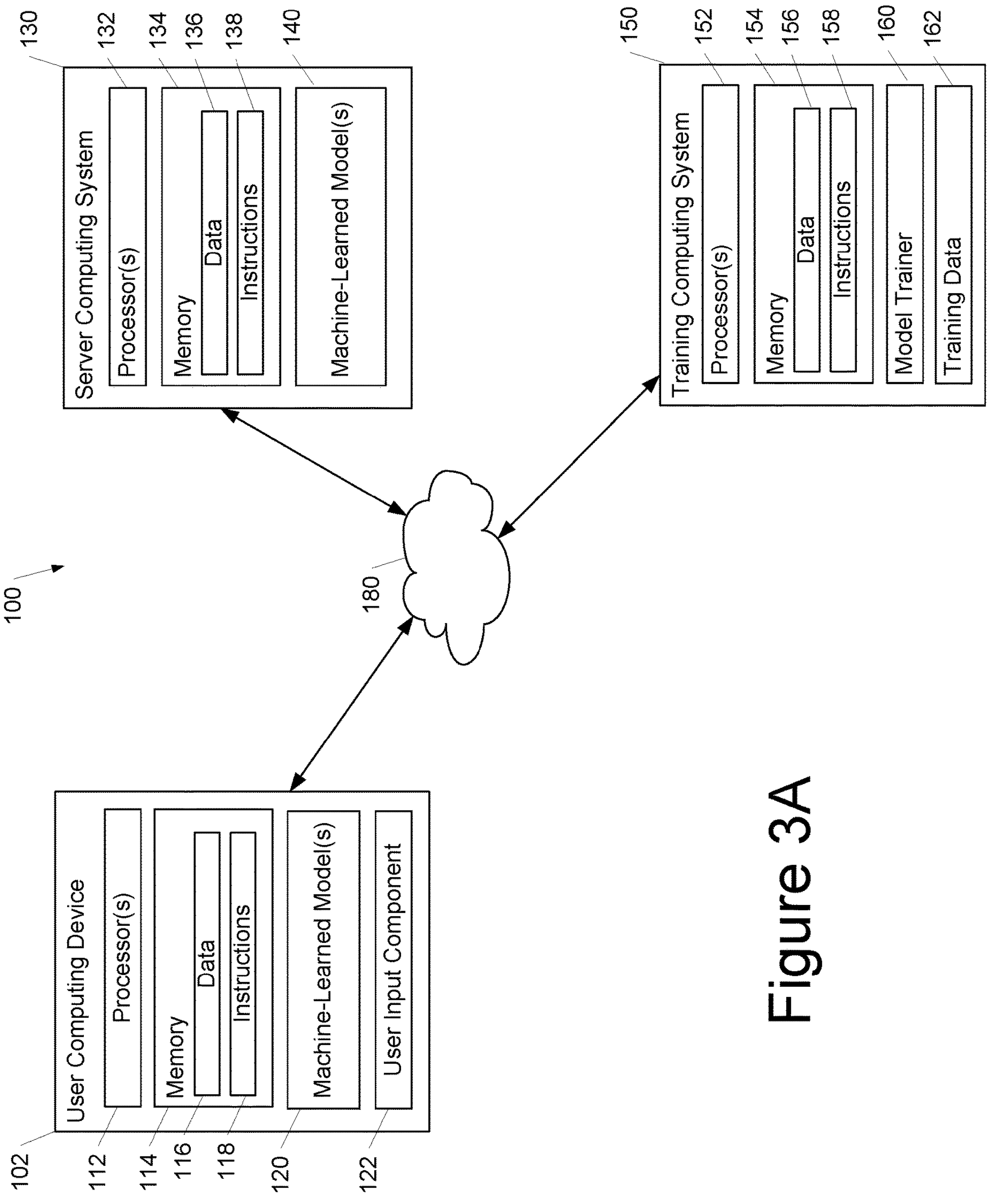
FIG. 3A depicts a block diagram of an example computing system according to example embodiments of the present disclosure.

FIG. 3A depicts a block diagram of an example computing system 100 according to example embodiments of the present disclosure. The system 100 includes a user computing device 102, a server computing system 130, and a training computing system 150 that are communicatively coupled over a network 180.

The user computing device 102 can be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing device 102 includes one or more processors 112 and a memory 114. The one or more processors 112 can be any suitable processing device (e.g., a processor core, a microprocessor, an ASIC, an FPGA, a controller, a microcontroller, etc.) and can be one processor or a plurality of processors that are operatively connected. The memory 114 can include one or more non-transitory computer-readable storage media, such as RAM, ROM, EEPROM, EPROM, flash memory devices, magnetic disks, etc., and combinations thereof. The memory 114 can store data 116 and instructions 118 which are executed by the processor 112 to cause the user computing device 102 to perform operations.

In some implementations, the user computing device 102 can store or include one or more disease detection models 120. For example, the disease detection models 120 can be or can otherwise include various machine-learned models such as neural networks (e.g., deep neural networks) or other types of machine-learned models, including non-linear models and/or linear models. Neural networks can include feed-forward neural networks, recurrent neural networks (e.g., long short-term memory recurrent neural networks), convolutional neural networks or other forms of neural networks. Example disease detection models 120 are discussed with reference to FIGS. 1A-2C.

In some implementations, the one or more disease detection models 120 can be received from the server computing system 130 over network 180, stored in the user computing device memory 114, and then used or otherwise implemented by the one or more processors 112. In some implementations, the user computing device 102 can implement multiple parallel instances of a single disease detection model 120 (e.g., to perform parallel disease detection across multiple frames of imagery).

Additionally or alternatively, one or more disease detection models 140 can be included in or otherwise stored and implemented by the server computing system 130 that communicates with the user computing device 102 according to a client-server relationship. For example, the disease detection models 140 can be implemented by the server computing system 140 as a portion of a web service (e.g., a disease detection service). Thus, one or more models 120 can be stored and implemented at the user computing device 102 and/or one or more models 140 can be stored and implemented at the server computing system 130.

The user computing device 102 can also include one or more user input components 122 that receives user input. For example, the user input component 122 can be a touch-sensitive component (e.g., a touch-sensitive display screen or a touch pad) that is sensitive to the touch of a user input object (e.g., a finger or a stylus). The touch-sensitive component can serve to implement a virtual keyboard. Other example user input components include a microphone, a traditional keyboard, or other means by which a user can provide user input.

The server computing system 130 includes one or more processors 132 and a memory 134. The one or more processors 132 can be any suitable processing device (e.g., a processor core, a microprocessor, an ASIC, an FPGA, a controller, a microcontroller, etc.) and can be one processor or a plurality of processors that are operatively connected. The memory 134 can include one or more non-transitory computer-readable storage media, such as RAM, ROM, EEPROM, EPROM, flash memory devices, magnetic disks, etc., and combinations thereof. The memory 134 can store data 136 and instructions 138 which are executed by the processor 132 to cause the server computing system 130 to perform operations.

In some implementations, the server computing system 130 includes or is otherwise implemented by one or more server computing devices. In instances in which the server computing system 130 includes plural server computing devices, such server computing devices can operate according to sequential computing architectures, parallel computing architectures, or some combination thereof.

As described above, the server computing system 130 can store or otherwise include one or more disease detection models 140. For example, the models 140 can be or can otherwise include various machine-learned models. Example machine-learned models include neural networks or other multi-layer non-linear models. Example neural networks include feed forward neural networks, deep neural networks, recurrent neural networks, and convolutional neural networks. Example models 140 are discussed with reference to FIGS. 1A-2C.

The user computing device 102 and/or the server computing system 130 can train the models 120 and/or 140 via interaction with the training computing system 150 that is communicatively coupled over the network 180. The training computing system 150 can be separate from the server computing system 130 or can be a portion of the server computing system 130.

The training computing system 150 includes one or more processors 152 and a memory 154. The one or more processors 152 can be any suitable processing device (e.g., a processor core, a microprocessor, an ASIC, an FPGA, a controller, a microcontroller, etc.) and can be one processor or a plurality of processors that are operatively connected. The memory 154 can include one or more non-transitory computer-readable storage media, such as RAM, ROM, EEPROM, EPROM, flash memory devices, magnetic disks, etc., and combinations thereof. The memory 154 can store data 156 and instructions 158 which are executed by the processor 152 to cause the training computing system 150 to perform operations. In some implementations, the training computing system 150 includes or is otherwise implemented by one or more server computing devices.

The training computing system 150 can include a model trainer 160 that trains the machine-learned models 120 and/or 140 stored at the user computing device 102 and/or the server computing system 130 using various training or learning techniques, such as, for example, backwards propagation of errors. For example, a loss function can be backpropagated through the model(s) to update one or more parameters of the model(s) (e.g., based on a gradient of the loss function). Various loss functions can be used such as mean squared error, likelihood loss, cross entropy loss, hinge loss, and/or various other loss functions. Gradient descent techniques can be used to iteratively update the parameters over a number of training iterations.

In some implementations, performing backwards propagation of errors can include performing truncated backpropagation through time. The model trainer 160 can perform a number of generalization techniques (e.g., weight decays, dropouts, etc.) to improve the generalization capability of the models being trained.

In particular, the model trainer 160 can train the disease detection models 120 and/or 140 based on a set of training data 162. The training data 162 can include, for example, images of anterior portions of eyes that have been labelled with a ground truth disease label.

In some implementations, if the user has provided consent, the training examples can be provided by the user computing device 102. Thus, in such implementations, the model 120 provided to the user computing device 102 can be trained by the training computing system 150 on user-specific data received from the user computing device 102. In some instances, this process can be referred to as personalizing the model.

The model trainer 160 includes computer logic utilized to provide desired functionality. The model trainer 160 can be implemented in hardware, firmware, and/or software controlling a general purpose processor. For example, in some implementations, the model trainer 160 includes program files stored on a storage device, loaded into a memory and executed by one or more processors. In other implementations, the model trainer 160 includes one or more sets of computer-executable instructions that are stored in a tangible computer-readable storage medium such as RAM, hard disk, or optical or magnetic media.

The network 180 can be any type of communications network, such as a local area network (e.g., intranet), wide area network (e.g., Internet), or some combination thereof and can include any number of wired or wireless links. In general, communication over the network 180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

FIG. 3A illustrates one example computing system that can be used to implement the present disclosure. Other computing systems can be used as well. For example, in some implementations, the user computing device 102 can include the model trainer 160 and the training dataset 162. In such implementations, the models 120 can be both trained and used locally at the user computing device 102. In some of such implementations, the user computing device 102 can implement the model trainer 160 to personalize the models 120 based on user-specific data.

Figure 3B:
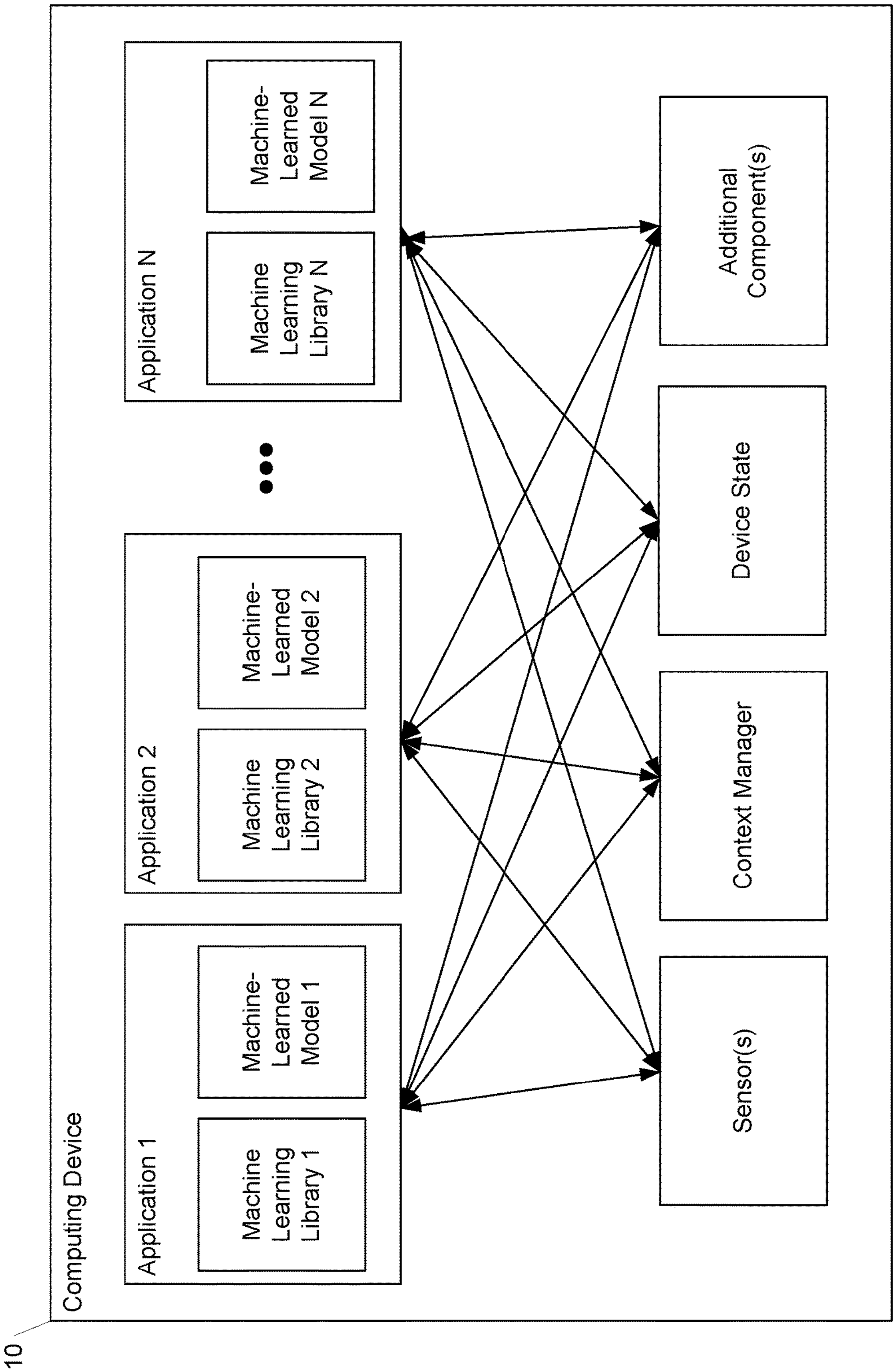
FIG. 3B depicts a block diagram of an example computing device according to example embodiments of the present disclosure.

FIG. 3B depicts a block diagram of an example computing device 10 that performs according to example embodiments of the present disclosure. The computing device 10 can be a user computing device or a server computing device.

The computing device 10 includes a number of applications (e.g., applications 1 through N). Each application contains its own machine learning library and machine-learned model(s). For example, each application can include a machine-learned model. Example applications include a text messaging application, an email application, a dictation application, a virtual keyboard application, a browser application, etc.

As illustrated in FIG. 3B, each application can communicate with a number of other components of the computing device, such as, for example, one or more sensors, a context manager, a device state component, and/or additional components. In some implementations, each application can communicate with each device component using an API (e.g., a public API). In some implementations, the API used by each application is specific to that application.

Figure 3C:
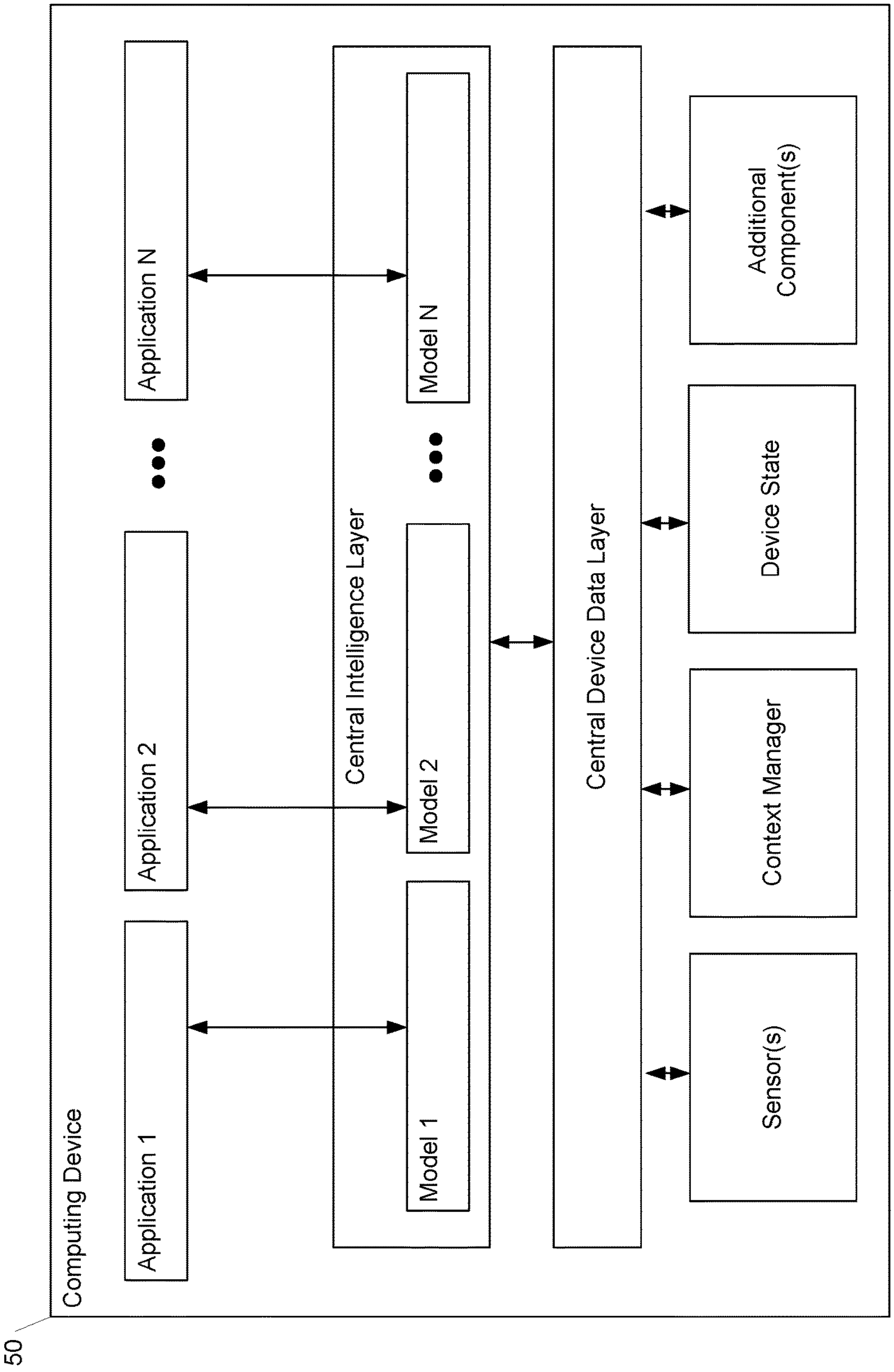
FIG. 3C depicts a block diagram of an example computing device according to example embodiments of the present disclosure.

FIG. 3C depicts a block diagram of an example computing device 50 that performs according to example embodiments of the present disclosure. The computing device 50 can be a user computing device or a server computing device.

The computing device 50 includes a number of applications (e.g., applications 1 through N). Each application is in communication with a central intelligence layer. Example applications include a text messaging application, an email application, a dictation application, a virtual keyboard application, a browser application, etc. In some implementations, each application can communicate with the central intelligence layer (and model(s) stored therein) using an API (e.g., a common API across all applications).

The central intelligence layer includes a number of machine-learned models. For example, as illustrated in FIG. 3C, a respective machine-learned model can be provided for each application and managed by the central intelligence layer. In other implementations, two or more applications can share a single machine-learned model. For example, in some implementations, the central intelligence layer can provide a single model for all of the applications. In some implementations, the central intelligence layer is included within or otherwise implemented by an operating system of the computing device 50.

The central intelligence layer can communicate with a central device data layer. The central device data layer can be a centralized repository of data for the computing device 50. As illustrated in FIG. 3C, the central device data layer can communicate with a number of other components of the computing device, such as, for example, one or more sensors, a context manager, a device state component, and/or additional components. In some implementations, the central device data layer can communicate with each device component using an API (e.g., a private API).

Additional Disclosure

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A computing system to perform multi-instance contrastive learning for improved analysis of medical imagery, the computing system comprising one or more processors and one or more non-transitory computer-readable media that collectively store instructions that, when executed by the one or more processors, cause the computing system to perform operations, the operations comprising:

obtaining, by the computing system, a set of medical training images that comprises a plurality of patient-specific image subsets, wherein each patient-specific image subset contains a plurality of different images that depict a same respective patient, wherein the set of medical training images are associated with a target domain;

for each of the plurality of patient-specific image subsets:

obtaining, by the computing system, a first medical image that depicts a patient and a second, different medical image that depicts the same patient;

processing, by the computing system, the first medical image with a machine-learned medical image analysis model to generate a first embedding for the first medical image, wherein the machine-learned medical image analysis model was pretrained with self-supervised pretraining on unlabeled natural images, wherein the unlabeled natural images are not a medical image dataset, wherein the unlabeled natural images comprise images that are not medical images, wherein pretraining comprises augmenting unlabeled images including color distortion, generating model-generated predictions associated with different augmented versions, and adjusting model parameters based on comparing model-generated predictions associated with different augmented versions of an unlabeled image;

processing, by the computing system, the second medical image with the machine-learned medical image analysis model to generate a second embedding for the second medical image; and modifying, by the computing system, one or more values of one or more parameters of the machine-learned medical image analysis model based at least in part on a loss function that evaluates a difference between the first embedding for the first medical image and the second embedding for the second medical image; and performing supervised fine-tuning on the machine-learned medical image analysis model using a set of labeled medical images.

2. The computing system of claim 1, wherein the machine-learned medical image analysis model comprises a machine-learned diagnostic model that is configured to generate one or more medical diagnostic predictions for an input image.

3. The computing system of claim 1, wherein the first medical image of the patient and the second medical image of the patient were captured from different viewing angles.

4. The computing system of claim 1, wherein the first medical image of the patient and the second medical image of the patient were captured under different lighting conditions.

5. The computing system of claim 1, wherein the first medical image of the patient and the second medical image of the patient depict different portions of a body of the patient.

6. The computing system of claim 1, wherein the first medical image of the patient and the second medical image of the patient were captured at separate medical treatment visits.

7. The computing system of claim 1, wherein the first medical image of the patient and the second medical image of the patient comprise two different frames of a video that depict a medical procedure.

8. The computing system of claim 1, wherein processing, by the computing system, the first medical image with a machine-learned medical image analysis model comprises augmenting, by the computing system, the first medical image and processing the augmented version of the first medical image with the machine-learned medical image analysis model to generate the first embedding.

9. The computing system of claim 8, wherein augmenting, by the computing system, the first medical image comprises cropping, by the computing system, the first medical image.

10. The computing system of claim 1, wherein the set of medical training images comprise: dermatological images, radiographic images, endoscopic images, ultrasound images, mammographic images, pathology images, posterior eye images, or three-dimensional scan images.

11. One or more non-transitory computer-readable media that collectively store instructions that, when executed by a computing system comprising one or more computing devices, cause the computing system to perform operations, the operations comprising:

obtaining, by the computing system, a set of medical training images that comprises a plurality of attribute-specific image subsets, wherein each attribute-specific image subset contains a plurality of different images that share a common attribute, wherein the set of medical training images are associated with a target domain;

for each of the plurality of attribute-specific image subsets:

obtaining, by the computing system, a first medical image and a second, different medical image that have the common attribute;

processing, by the computing system, the first medical image with a machine-learned medical image analysis model to generate a first embedding for the first medical image, wherein the machine-learned medical image analysis model was pretrained with self-supervised pretraining on unlabeled natural images, wherein the unlabeled natural images are not a medical image dataset, wherein the unlabeled natural images comprise images that are not medical images, wherein pretraining comprises augmenting unlabeled images including color distortion, generating model-generated predictions associated with different augmented versions, and adjusting model parameters based on comparing model-generated predictions associated with different augmented versions of an unlabeled image;

processing, by the computing system, the second medical image with the machine-learned medical image analysis model to generate a second embedding for the second medical image; and modifying, by the computing system, one or more values of one or more parameters of the machine-learned medical image analysis model based at least in part on a loss function that evaluates a difference between the first embedding for the first medical image and the second embedding for the second medical image; and performing supervised fine-tuning on the machine-learned medical image analysis model using a set of labeled medical images.

12. The one or more non-transitory computer-readable media of claim 11, wherein at least one of the attribute-specific image subsets contains a plurality of different images that depict a plurality of different patients diagnosed with a common medical condition.

13. The one or more non-transitory computer-readable media of claim 11, wherein at least one of the attribute-specific image subsets contains a plurality of different images that depict a plurality of body parts of a common patient that exhibit a common medical condition.

14. The computing system of claim 1, wherein the unlabeled natural images comprises images which depict common real world scenes, and wherein training on the set of medical training images and fine-tuning on the set of labeled medical images are at least one of task-specific or dataset specific unlike the self-supervised pretraining on unlabeled natural images.

* * * * *